United States Patent [19]
Sakura, Jr.

[11] 4,214,587
[45] Jul. 29, 1980

[54] ANASTOMOSIS DEVICE AND METHOD

[76] Inventor: Chester Y. Sakura, Jr., 6417 Esther NE., Albuquerque, N. Mex. 87109

[21] Appl. No.: 11,448

[22] Filed: Feb. 12, 1979

[51] Int. Cl.$^2$ .............................................. A61B 17/04
[52] U.S. Cl. ................................. 128/334 R; 285/239
[58] Field of Search ................... 128/243, 326, 334 R, 128/335, 335.5, 340, 345, 334 C; 285/239, 321, 397

[56] References Cited
U.S. PATENT DOCUMENTS

| | | | |
|---|---|---|---|
| 2,453,056 | 11/1948 | Zack | 128/334 C |
| 3,155,095 | 11/1964 | Brown | 128/334 C |
| 3,221,746 | 12/1965 | Noble | 128/334 R |
| 3,657,744 | 4/1972 | Ersek | 128/334 R |
| 3,774,615 | 11/1973 | Lim et al. | 128/334 C |
| 3,842,441 | 10/1974 | Kaiser | 128/334 R |
| 3,908,662 | 9/1975 | Razgulov et al. | 128/334 R |

*Primary Examiner*—C. Fred Rosenbaum
*Attorney, Agent, or Firm*—Woodard, Weikart, Emhardt & Naughton

[57] ABSTRACT

A preferred embodiment of the anastomosis device comprises a cylindrical, radially resilient spring upon which is attached a number of outwardly extending barbs. The radial spring action significantly simplifies the anastomosis procedure and in addition allows the mended portion of the blood vessel to pulsate in a fashion similar to that of the pulsatile action of an unmended vessel. The barbs attach the device to the blood vessel thus maintaining its position securely. The disclosed anastomosis device is recommended for rejoining small blood vessels where a simple, reliable alternative to micro-suturing techniques is desirable. In the anastomosis method of the present invention a cylindrical, radially resilient spring is compressed and placed about one end of a vessel. The second end of the vessel is then placed about the spring and the compression is released.

29 Claims, 9 Drawing Figures

ANASTOMOSIS DEVICE AND METHOD

BACKGROUND OF THE INVENTION

1. Field of the Invention

This invention relates to anastomosis devices and methods of anastomosis and more particularly, though not exclusively, relates to the anastomosis of small blood vessels in the human body.

2. Brief Description of the Prior Art

Accurate and complete anastomosis methods are necessary for successful microvascular surgery. It is often important that the anastomosis be performed in a minimal amount of time in order that tissue damage be avoided, that anaesthesia time is minimized and that the healing process be begun as soon as practicable. The anastomosis should provide a blood-tight seal, yet maintain good patency for blood flow. The presence of any material on the inside of the vessel should preferably be avoided as it can provide a nidus for clot formation. It is also desirable that the blood vessel have the ability to maintain a certain degree of its normal pulsatile action at the point of anastomosis. In addition, anastomosis must often be performed on blood vessels with diameters as small as one millimeter or less, therefore a successful anastomosis technique should be adaptable to such small dimensions.

The refinements of technique in microvascular surgery have developed in two directions. The first approach is the use of microsuture techniques. These surgical techniques have advanced with the aid of the development of operating microscopes, microsutures and microinstruments. They produce very accurate anastomosis and yield good patency. However, the techniques have not been widely used because they not only have the disadvantage of being time consuming, but they also have the disadvantage of requiring an extremely high degree of technical skill. The presence of suture material in the interior of a blood vessel can also present a nidus for clot formation.

The second approach has been in the direction of various mechanical devices or glues which attempt to circumvent the exacting skill and prolonged time required for the suturing techniques. The glues have generally been unsuccessful because of complications involving tissue toxicity and reaction. Stapling techniques have been cumbersome and have been difficult to use on vessels under 2 mm. in size. Other devices have included various tubes, flanges and rings. The rigidity of these devices has presented a problem of functional obstruction during pulsatile flow. The necessity for either everting one end of the vessel or stretching it over the rigid devices makes these anastomosis methods more difficult for smaller vessels.

Zack U.S. Pat. No. 2,453,056 is one such rigid anastomosis device. It is tubular in structure, has a longitudinal slot which permits partial compression and has ring-like clamps which slide over the structure to maintain the vessels in position. Upon compression, the longitudinal slot causes reduction in the surface of the cylindrically shaped device to occur only at the position of the slot and not uniformly about the cylinder. Moreover, the compression of the ring-like clamps may adversely affect the health of the compressed tissue. The Zack device does not have the capability of contraction and expansion during pulsatile flow. Lastly, the ring-like clamps can potentially slide off of the device and thus disrupt the anastomotic mend.

Brown U.S. Pat. No. 3,155,095 and Noble U.S. Pat. No. 3,221,746 are two more examples of rigid anastomosis devices. The Brown device is composed of absorbable material over which the ends of the vessels are stretched and has external clamps similar to the Zach patent. Noble uses hooks as a means for attachment. Both of these devices require the stretching of the ends of the blood vessels over the rigid devices and has considerable exposed surface area in the interior portion of the mended blood vessel. This exposure can provide a nidus for clot formation, can cause obstruction of normal blood flow and their rigidity prevents the vessel from pulsating normally.

Razgulov U.S. Pat. No. 3,908,662 is an eversion device and vascular stapling instrument. This device illustrates the state of the art in vascular stapling techniques for purposes of anastomosis. A portion of the instrument includes a rigid, slotted tubular structure (somewhat resembling the Zack device) that is used as a bushing about which the end of a vessel is everted.

Bucalo U.S. Pat. No. 3,938,528 is another rigid anastomosis device. It uses hooks as a means of attachment and, when in place, is entirely in the internal portion of the blood vessel. As with other rigid devices, this device has no ability to accomodate pulsatile expansion to any degree.

Some non-analogous prior art shows the existence of "s"-shaped metal wire, cylindrical tension devices (see, e.g., Wilkening U.S. Pat. No. 2,293,450). Such devices would not be suitable for use as anastomosis devices even if they had been considered for a number of reasons: (1) They generally are not made of a material which is suitable for implantation into the body. (2) They generally are much too large, not only in diameter, but also in some instances, in the number of "s"-shaped loops. (3) They generally have an undesirable height to diameter ratio. (4) They generally do not have associated barbs which could serve to retain either a snare loop or blood vessels.

Wells U.S. Pat. No. 1,672,591 is a nostril dilator that is essentially a lateral spring mechanism comprising a series of loops. Although it is a spring-like device, this patent is considerably different in structure from the preferred embodiment of the present invention in that it is not radially resilient and is comprised of loops instead of "s"-shaped elements. In use of the Wells device, the outward pressure supplied is only in two directions and the Wells device itself would be much too large to be used with a blood vessel. The Wells device also does not have associated barbs which could serve to retain either a snare loop or blood vessels.

SUMMARY OF THE INVENTION

Broadly described, a preferred embodiment of the present invention is a cylindrical, radially resilient spring having "s"-shaped elements of resilient wire. Barbs are attached to the spring and project outwardly for the purpose of securely attaching the device to the blood vessel.

There are numerous advantages which this device has over previous anastomosis techniques. It does not possess the disadvantage of requiring an extremely high degree of technical skill to be utilized effectively, which is a problem with micro-suturing techniques. Nor is it time consuming which is another problem with microsuturing as opposed to the various stapling techniques.

This device can be used effectively on vessels of extremely small diameter.

Because of its radial resiliency, the preferred embodiment can be easily applied to small vessels without excessive stretching of the vessels.

The ready resiliency of the preferred embodiment will allow the device to contract and expand with the pulsating action of a mended vessel. This is a significant aid in avoiding stenosis and blood flow obstruction. It is a significant advance over the prior art devices which are rigid in nature and thus present a functional obstruction during the pulsatile flow of the vessel.

The preferred embodiment of the invention can be used effectively where only a small portion of the vessel to be mended is exposed.

Because the preferred embodiment of the invention has no exposed surfaces in the interior of the blood vessel, it does not create a nidus for clot formation in the intima portion of the mended vessel.

DETAILED DESCRIPTION OF THE PREFERRED EMBODIMENT

Figure 1:
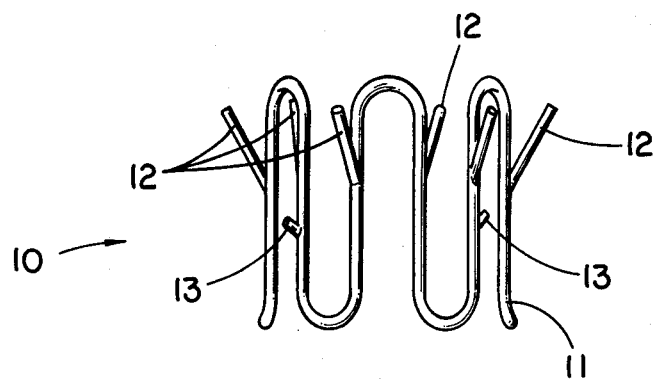
FIG. 1 is a side view of a preferred embodiment of the present invention showing the spring structure and outwardly projecting barbs.

The preferred embodiment 10 of the invention is illustrated in FIG. 1. It comprises a continuous filament 11 of resilient dental wire which generally runs in an "s"-shaped pattern about the circumference of a cylinder. The "s" shaped pattern is used because it easily compresses radially and it does not have sharp edges that could cause tissue damage. The continuous filament 11 is loop-free because loops would have a tendency to pinch tissue when the device compresses and expands. The exposed surfaces of the preferred embodiment must be compatible for implantation into the human body. Dental wire is used because of its compatability and because it can be easily shaped into the desired configurations of the preferred embodiment.

Barbs 12 are attached to the spring and project outwardly at an angle of about 30°. These barbs act as a means of attaching the device to the vessels and are angularly directed toward one end of the preferred embodiment. A second set of barbs 13 are set at a longitudinal distance from the first set and project radially outward at an angle about 90°. The barbs 13 are used as an aid in compressing the anastomosis device. They act as a guide for a snare loop 20 and thus prevent unintentional slippage of the loop off of the spring.

Figure 2:
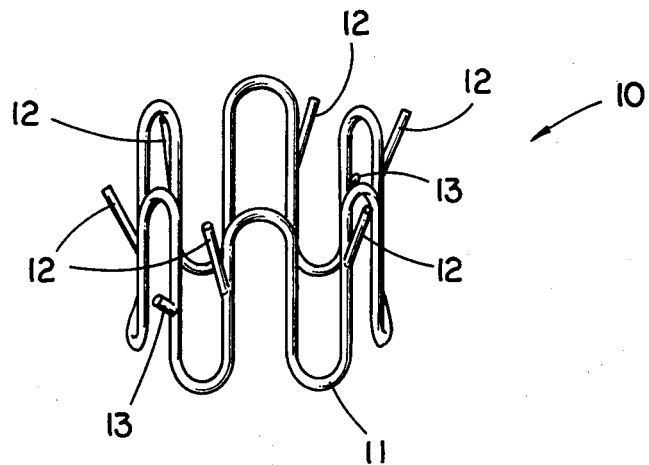
FIG. 2 is an isometric perspective view of the device of FIG. 1.

FIG. 2 is an isometric perspective view of the preferred embodiment, showing portions that were not exposed to view in FIG. 1. The diameter is 4 millimeters, which is within the range of diameters of the human blood vessel. The device is well suited to be made with a diameter of from 0.5 to 2 mm. which is a size for which there are limited alternative anastomosis techniques. It is preferred that the diameter be slightly larger (i.e. 25%) than the size of the vessel to be mended. Diameters greater than one centimeter are impractical, because vessels of such a large diameter are rare and those that do exist are easily mended by other anastomosis techniques such as suturing.

In the preferred embodiment there are twelve portions which run generally in a longitudinal direction. The number of longitudinal portions may vary, depending upon the relative size of the vessel to be mended, however in most practical applications the number will be at least 6 but not more than 32.

The diameter to height ratio of the preferred embodiment is approximately one. Ratios greater than three tend to produce an unstable device that would have a tendancy to accidently release its compression.

It is preferred that anastomosis devices according to the invention be compressible to at least about 80% of its original uncompressed diameter without being deformed to the extent that it will not return essentially to its original uncompressed size. Radial resiliency is required (1) in order for the anastomosis device to be easily implanted (2) in order to make the anastomosis blood tight, (3) in order to make the anastomosis larger than the parent vessel itself (to minimize the possibility of constriction and clot formation) and also (4) in order to allow the anastomosis device to contract and expand with the pulsatile action of the vessel after it has been implanted. The preferred embodiment can be compressed to 50% of its original size without permanent deformation.

Figure 3:
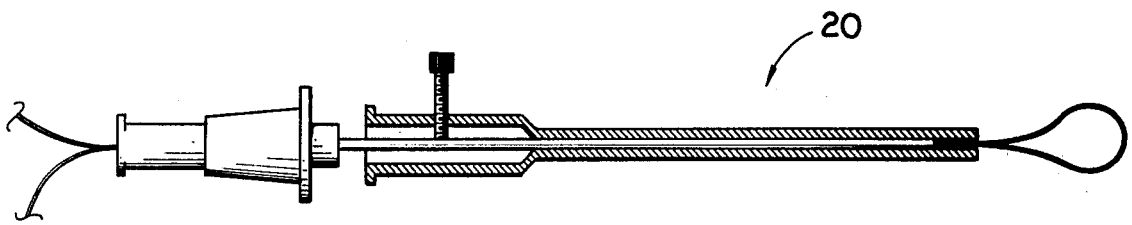
FIG. 3 is a side view of a surgical snare loop which is a preferred means of compression of the device of FIG. 1.
Figure 4:
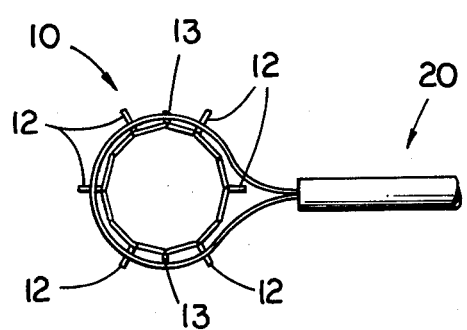
FIG. 4 is an elevational view of the end of the snare loop of FIG. 3 loosely in position about the device of FIG. 1.
Figure 5:
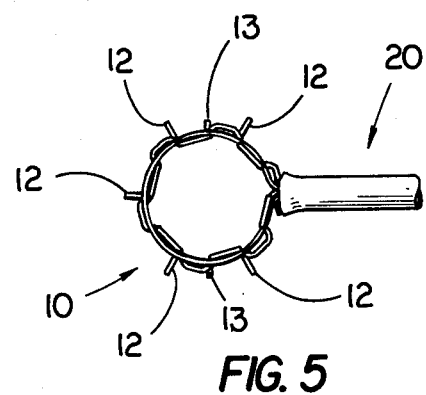
FIG. 5 is an elevational view of the end of the snare loop of FIG. 3 tightened about and in a position ready to compress the device of FIG. 1.

FIG. 3 is a diagram of a surgical snare loop 20 which is the preferred removable means of compressing and releasing the tension of the preferred embodiment of the invention. FIG. 4 illustrates the manner in which the line 21 of the snare loop is wrapped about the preferred embodiment. FIG. 5 is an elevational view of the surgical snare loop 20 that has been tightened about a preferred embodiment and thus is in a position whereby it can compress the device.

Figure 6:
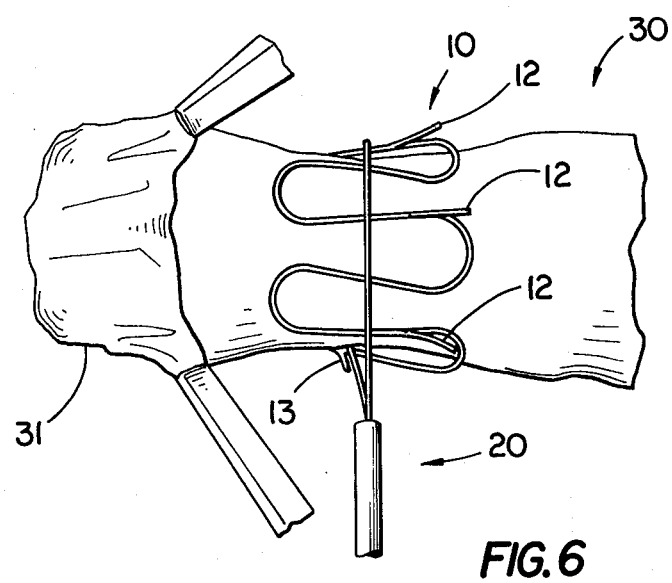
FIG. 6 shows the device of FIG. 1 compressed by the snare of FIG. 3 about the end of one vessel and the beginning of eversion of the end of the vessel over the device.
Figure 7:
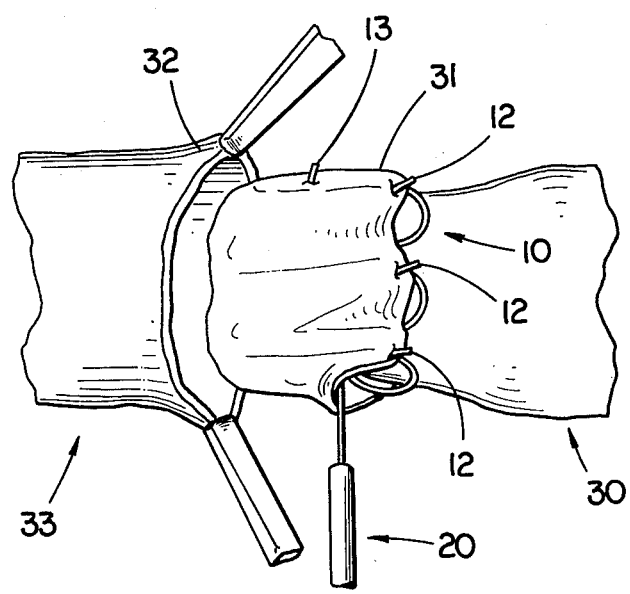
FIG. 7 shows the completed eversion and attachment of the end of the vessel to the device, and beginning of placement of the end of the second vessel over the combination.
Figure 8:
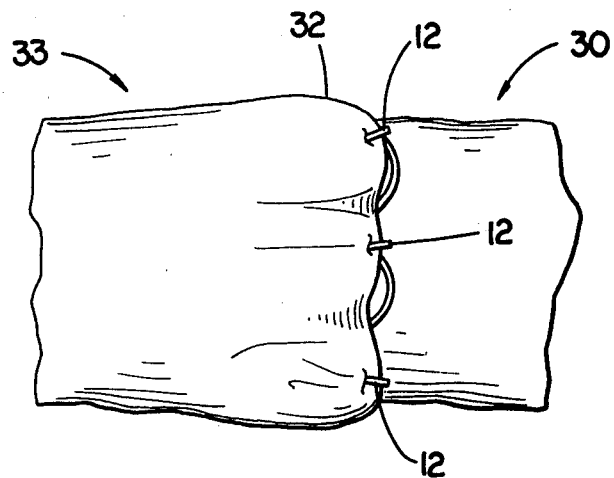
FIG. 8 is an external side view of the completed anastomosis produced by the steps shown in FIGS. 5, 6 and 7.

A specific example of the preferred embodiment of the anastomosis process is as follows. After a snare loop is placed about the anastomosis device of FIG. 1, the device is then slipped around the end of a first vessel. The spring is then compressed by the snare loop and the end of the vessel is everted and placed around the device. This compressing simplifies the anastomosis by minimizing or eliminating the need to stretch the vessel ends. To accomplish this, the anastomosis device is compressed to at most 80% of its original uncompressed diameter. FIG. 6 shows the preferred embodiment in its compressed state about the blood vessel 30 and the end of the vessel 31 in the process of being everted about the device. The everted cuff of the vessel is then attached to the barbs 12 on the device. The end 32 of the second vessel 33 is next placed around the combination of the device and the everted end of the first vessel. FIG. 7 shows the completed eversion and attachment of the first vessel and the beginning of the placement of the second vessel end around the combination. The second vessel end is then attached to the barbs 12 of the device. The compression from the snare loop is released and the snare loop line removed thus allowing the device to expand to approximately its original size. FIG. 8 illustrates the anastomosis after the snare line loop has been removed.

Figure 9:
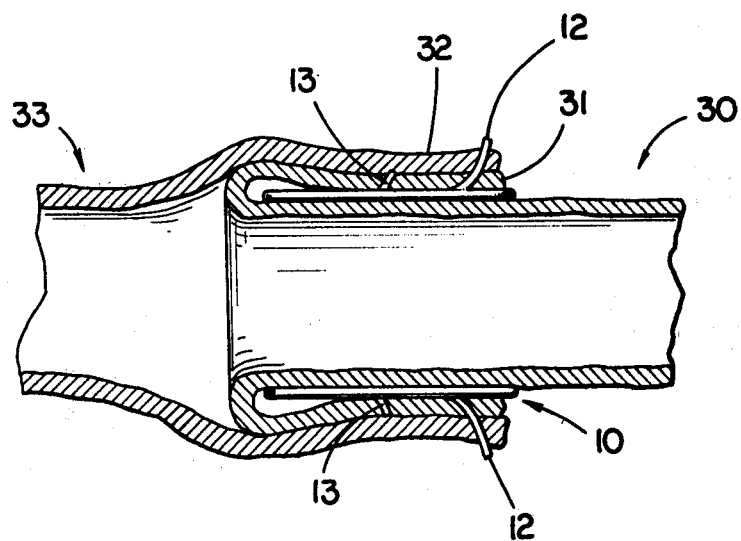
FIG. 9 is a cross-sectional view of the completed anastomosis of FIG. 8.

FIG. 9 illustrates a cross-sectional view of the completed anastomosis. The vessel ends 31 and 32 are attached to each other by the barbs 12. The device 10 is positioned between the exterior of the first vessel 30 and the first vessel's everted cuff 31, thus no portion of the device is exposed to the lumen of the mended vessel. Because of the device's radial resiliency, it contracts and expands with the pulsatile action of the vessel.

Thirty-seven femoral arteries in nineteen dogs were sectioned and repaired by the above described procedure. The vessels ranged in diameter from 2.5 mm. to 3.8 mm. Seven of the anastomoses were followed for 1 month, ten for 3 months, fourteen for 6 months, and six for 1 year.

The arteries were examined for thrombosis or narrowing. There was only one occlusion found in the thirty-seven operated arteries. No negative tissue reaction was discovered. Bursting and shearing tests were performed on two of the anastomoses. Using a spring strain gauge as a tensilometer, the breaking points of the two anastomoses were 800 and 1500 grams. The bursting pressure test, performed with a mercury manometer, showed the anastomoses to withstand pressures up to 1000 mm/Hg.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An anastomosis device comprising:
   (a) an essentially cylindrical, radially resilient spring, the exposed surfaces of said spring comprising material that is compatible for implantation into the human body and said spring having a cylindrical diameter of not more than 1 cm. and
   (b) a plurality of barbs joined to and extending outwardly from said spring.

2. The anastomosis device of claim 1 in which the spring comprises at least 6 but not more than 32 portions that each runs generally in a longitudinal direction.

3. The anastomosis device of claim 1 in which the spring includes a series of "s"-shaped elements.

4. The anastomosis device of claim 1 which also comprises a removable means of compressing and releasing said spring.

5. The anastomosis device of claim 1 in which the spring can be compressed to 80% of its diameter without preventing it from resiliently returning to its original uncompressed size.

6. The anastomosis device of claim 1 in which said plurality of barbs are angularly directed toward one end of the cylinder.

7. The anastomosis device of claim 6 which also comprises a second plurality of barbs joined to and extending generally radially outward from said spring and positioned at a longitudinal distance from said first plurality of barbs.

8. The anastomosis device of claim 7 in which said first plurality of barbs project outwardly at an angle of about 30° and said second plurality of barbs project outwardly at an angle of about 90°.

9. The anastomosis device of claim 1 in which said spring comprises a resilient filament.

10. The anastomosis device of claim 9 in which said filament is a metal wire.

11. The anastomosis device of claim 9 in which said filament is dental wire.

12. The anastomosis device of claim 9 in which the spring comprises at least 6 but not more than 32 portions that each runs generally in a longitudinal direction.

13. The anastomosis device of claim 12 in which said filament is a metal wire.

14. The anastomosis device of claim 13 in which said plurality of barbs are angularly directed toward one end of the cylinder.

15. The anastomosis device of claim 14 in which said spring can be compressed to 80% of its diameter without preventing it from resiliently returning to its original uncompressed size.

16. The anastomosis device of claim 15 in which said wire is continuous and forms a series of "s"-shaped elements.

17. The anastomosis device of claim 16 which also comprises a second plurality of barbs joined to and extending generally radially outward from said spring and positioned at a longitudinal distance from said first plurality of barbs.

18. The anastomosis device of claim 17 which also comprises a removable means for maintaining radial compression and releasing radial compression of said spring.

19. An anastomosis device comprising an essentially cylindrical, loop-free, radially resilient spring made of a resilient filament having at least 6 but not more than 32 portions that each runs generally in a longitudinal direction, the exposed surfaces of said spring comprising material that is compatible for implantation beneath the skin of the human body and said spring having an uncompressed cylindrical diameter of not more than 1 cm. and having a diameter to height ratio of not more than approximately 3 in the uncompressed state.

20. The anastomosis device of claim 19 in which said filament is a metal wire.

21. The anastomosis device of claim 20 in which said spring can be compressed to 80% of its diameter without preventing it from resiliently returning to its original uncompressed size.

22. The anastomosis device of claim 21 in which said wire is continuous and forms a series of "s"-shaped elements.

23. The anastomosis device of claim 19 in which said wire is continuous and forms a series of "s"-shaped elements.

24. A process of anastomosis comprising of the steps of:
   (a) radially compressing a radially resilient, essentially cylindrical spring;
   (b) while maintaining said spring in a radially compressed state:

(1) placing the end of a first vessel over said radially compressed spring and
(2) placing the end of a second vessel over said radially compressed spring; and (c) after said placing of said second vessel, releasing the radial compression on said spring.

25. The process of claim 24 in which said radial compressing is done with sufficient force to result in a reduction in diameter of the spring to 80% or less of the uncompressed diameter of the spring.

26. The process of claim 25 in which said everting is done to an extent that the first vessel extends completely over the radially compressed spring.

27. A process of anastomosis comprising of the steps of:
(a) placing a radially resilient essentially cylindrical spring around the end of a first vessel;
(b) radially compressing the spring while around the first vessel;
(c) while maintaining the spring in a radially compressed state:
(1) everting the end of the first vessel over the radially compressed spring and
(2) after said everting, placing the end of a second vessel over the combination of the spring and everted first vessel; and
(d) after said placing of said second vessel, releasing the radial compression on the spring.

28. The process of claim 27 in which said radial compressing is done with sufficient force to result in a reduction in diameter of the spring to 80% or less of the uncompressed diameter of the spring.

29. The process of claim 27 in which said slipping of the second vessel is done to an extent that the second vessel extends completely over the radially compressed spring.

* * * * *